US012697386B2

(12) United States Patent
Weiner

(10) Patent No.: US 12,697,386 B2
(45) Date of Patent: Aug. 4, 2026

(54) NUCLEIC ACID ANTIBODY CONSTRUCTS FOR USE AGAINST EBOLA VIRUS

(71) Applicant: THE WISTAR INSTITUTE OF ANATOMY AND BIOLOGY, Philadelphia, PA (US)

(72) Inventor: David Weiner, Merion, PA (US)

(73) Assignee: The Wistar Institute of Anatomy and Biology, Phildelphia (PA)

( * ) Notice: Subject to any disclaimer, the term of this patent is extended or adjusted under 35 U.S.C. 154(b) by 1257 days.

(21) Appl. No.: 16/966,503

(22) PCT Filed: Jan. 31, 2019

(86) PCT No.: PCT/US2019/015984
§ 371 (c)(1),
(2) Date: Jul. 31, 2020

(87) PCT Pub. No.: WO2019/152607
PCT Pub. Date: Aug. 8, 2019

(65) Prior Publication Data
US 2021/0047388 A1     Feb. 18, 2021

Related U.S. Application Data

(60) Provisional application No. 62/624,308, filed on Jan. 31, 2018.

(51) Int. Cl.
*A61K 39/42*       (2006.01)
*A61K 48/00*       (2006.01)
*A61P 31/14*       (2006.01)
*C07K 16/10*       (2006.01)

(52) U.S. Cl.
CPC ............ *A61K 39/42* (2013.01); *A61K 48/005* (2013.01); *A61P 31/14* (2018.01); *C07K 16/10* (2013.01)

(58) Field of Classification Search
CPC ....... A61K 39/42; A61K 48/005; A61P 31/14; C07K 16/10
See application file for complete search history.

(56) References Cited

U.S. PATENT DOCUMENTS

| | | | | |
|---|---|---|---|---|
| 9,631,191 | B2 * | 4/2017 | Zdanovsky | ........ G01N 33/6845 |
| 11,896,654 | B2 * | 2/2024 | Weiner | .............. A61K 31/7088 |
| 12,162,925 | B2 * | 12/2024 | Weiner | .................. C07K 16/10 |
| 2017/0355751 | A1 | 12/2017 | Kyratsous | |
| 2019/0091322 | A1 * | 3/2019 | Weiner | .................. A61P 31/12 |
| 2021/0188947 | A1 * | 6/2021 | Weiner | .............. C07K 16/1027 |

FOREIGN PATENT DOCUMENTS

WO      2017165460 A1      9/2017

OTHER PUBLICATIONS

Malvy et al. ("Ebola virus disease." The Lancet 393.10174 (2019): 936-948).*
Schroeder et al. (J Allergy Clin Immunol 2010, 125:S41-S52).*
Lloyd et al. (Protein Engineering, Design & Selection 2009, 22:159-168; see, e.g., Discussion).*
Baseler et al. ("The pathogenesis of Ebola virus disease." Annual Review of Pathology: Mechanisms of Disease 12.1 (2017): 387-418).*
Moekotte et al. ("Monoclonal antibodies for the treatment of Ebola virus disease." Expert opinion on investigational drugs 25.11 (2016): 1325-1335.).*
Rudikoff et al. (Proc Natl Acad Sci USA 1982 vol. 79 p. 1979.*
Sela-Culang, Inbal, Vered Kunik, and Yanay Ofran. "The structural basis of antibody-antigen recognition." Frontiers in immunology 4 (2013): 302.*
International Search Report and Written Opinion issued in App. No. PCT/US19/15984, mailing date Jul. 8, 2019, 6 pages.

* cited by examiner

*Primary Examiner* — Kimberly Chong
(74) *Attorney, Agent, or Firm* — Riverside Law LLP

(57) ABSTRACT

Disclosed herein is a composition including a recombinant nucleic acid sequence that encodes an antibody to an Ebola viral antigen. Also disclosed herein is a method of generating a synthetic antibody in a subject by administering the composition to the subject. The disclosure also provides a method of preventing and/or treating an Ebola virus infection in a subject using said composition and method of generation.

12 Claims, No Drawings

Specification includes a Sequence Listing.

SEQUENCE LISTING

```
<160> NUMBER OF SEQ ID NOS: 14

<210> SEQ ID NO 1
<211> LENGTH: 471
<212> TYPE: PRT
<213> ORGANISM: Artificial Sequence
<220> FEATURE:
<223> OTHER INFORMATION: DMAb-11 Heavy Chain

<400> SEQUENCE: 1

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Val
        35                  40                  45

Arg Ser Asn Tyr Leu Ser Trp Val Arg Gln Ala Pro Gly Lys Gly Leu
    50                  55                  60

Glu Trp Val Ser Leu Ile Tyr Ser Gly Gly Leu Thr Ala Tyr Ala Asp
65                  70                  75                  80

Ser Val Glu Gly Arg Phe Thr Ile Ser Arg Asp Asn Ser Lys Asn Thr
                85                  90                  95

Leu Tyr Leu Gln Met Asn Ser Leu Arg Val Glu Asp Thr Ala Leu Tyr
            100                 105                 110

Tyr Cys Ala Arg Val Ala Ser Ser Ala Gly Thr Phe Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190
```

-continued

```
Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 2
<211> LENGTH: 1413
<212> TYPE: DNA
<213> ORGANISM: Artificial Sequence
<220> FEATURE:
<223> OTHER INFORMATION: DMAb-11 Heavy Chain

<400> SEQUENCE: 2

```
atggactgga cctggagaat cctgttcctg gtggcagcag caaccggaac acacgcagag        60
gtgcagctgg tggagagcgg cggcggcctg atccagcctg gcggcagcct gaggctgtcc       120
tgcgcagcat ctggatttgc cgtgcggagc aactacctgt cctgggtgcg ccaggcacca       180
ggcaagggcc tggagtgggt gtctctgatc tacagcggcg gcctgaccgc atatgcagac       240
tccgtggagg gcaggttcac catctccaga dataactcta agaatacact gtatctgcag       300
atgaatagcc tgcgggtgga ggacaccgcc ctgtactatt gcgcccgcgt ggccagctcc       360
gccggcacat tctactatgg catggacgtg tggggccagg gcaccacagt gaccgtgtct       420
agcgccagca caaagggacc atccgtgttt ccactggcac cctcctctaa gtccacctct       480
```

-continued

```
ggcggcacag ccgccctggg ctgtctggtg aaggattact tcccagagcc cgtgaccgtg    540
tcttggaaca gcggcgccct gacctccgga gtgcacacat ttccagccgt gctgcagagc    600
tccggcctgt acagcctgtc tagcgtggtg accgtgccct cctctagcct gggcacccag    660
acatatatct gcaacgtgaa tcacaagcca tccaatacaa aggtggacaa gaaggtggag    720
cccaagtctt gtgataagac ccacacatgc cctccctgtc ctgcaccaga gctgctgggc    780
ggcccaagcg tgttcctgtt ccacccaag cctaaggaca ccctgatgat cagcaggacc    840
cccgaggtga catgcgtggt ggtggacgtg tcccacgagg accccgaggt gaagtttaac    900
tggtacgtgg atggcgtgga ggtgcacaat gccaagacaa agcccaggga ggagcagtac    960
aactctacct atagagtggt gagcgtgctg acagtgctgc accaggactg gctgaacggc    1020
aaggagtata gtgcaaggt gtctaataag gccctgcccg cccctatcga gaagaccatc    1080
agcaaggcca agggccagcc tagggagcca caggtgtaca cactgcctcc atctagagac    1140
gagctgacca gaaccaggt gagcctgaca tgtctggtga agggcttcta tcctagcgat    1200
atcgccgtgg agtgggagtc caatggccag ccagagaaca attacaagac cacacccct    1260 gtgctggact ccgatggctc tttctttctg tattccaagc tgaccgtgga taagtctaga    1320
tggcagcagg gcaacgtgtt tagctgttcc gtgatgcacg aggccctgca caatcactac    1380
acacagaagt ctctgagcct gtcccctggc aag    1413
```

<210> SEQ ID NO 3
<211> LENGTH: 239
<212> TYPE: PRT
<213> ORGANISM: Artificial Sequence
<220> FEATURE:
<223> OTHER INFORMATION: DMAb-11 Light Chain

<400> SEQUENCE: 3

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Arg Ser Leu Ser
            20                  25                  30

Val Thr Pro Gly Glu Pro Ala Ser Ile Ser Cys Arg Ser Ser Gln Ser
        35                  40                  45

Leu Leu His Arg Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Ser Trp Thr Phe Gly Gln Gly Thr
        115                 120                 125

Lys Val Glu Ile Lys Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190
```

-continued

```
Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 4
<211> LENGTH: 717
<212> TYPE: DNA
<213> ORGANISM: Artificial Sequence
<220> FEATURE:
<223> OTHER INFORMATION: DMAb-11 Light Chain

<400> SEQUENCE: 4
atggtgctgc agacccaggt gttcatctct ctgctgctgt ggatcagcgg cgcctacggc     60
gacatcgtga tgacccagtc cccacggagc ctgtccgtga caccaggaga gccagcatct    120
atcagctgcc ggagctccca gagcctgctg caccgcaacg ctacaatta tctggattgg    180 tacctgcaga gcctggcca gtccccacag ctgctgatct atctgggctc caacagggca    240
tctggagtgc cagacagatt ctccggctct ggcagcggaa ccgacttcac cctgaagatc    300
tctagggtgg aggccgagga cgtgggcgtg tactattgca tgcaggccct gcagaccccc    360
agctggacat cggccaggg caccaaggtg gagatcaaga cagtggccgc cccttccgtg    420
ttcatctttc cccttctga cgagcagctg aagagcggca gcctccgt ggtgtgcctg    480 ctgaacaact ctaccctag agaggccaag gtgcagtgga aggtggataa cgccctgcag    540
tccggcaatt ctcaggagag cgtgaccgag caggactcca aggattctac atatagcctg    600
tctagcaccc tgacactgtc caaggccgat tacgagaagc acaaggtgta tgcatgcgag    660
gtgacccacc agggcctgtc ctctcccgtg acaaagagct ttaatcgcgg cgagtgt    717

<210> SEQ ID NO 5
<211> LENGTH: 473
<212> TYPE: PRT
<213> ORGANISM: Artificial Sequence
<220> FEATURE:
<223> OTHER INFORMATION: DMAb-30 Heavy Chain

<400> SEQUENCE: 5

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Thr Lys
            20                  25                  30

Pro Gly Ala Ser Val Lys Val Ser Cys Lys Ala Ser Gly Tyr Thr Phe
        35                  40                  45

Thr Thr Tyr Tyr Met His Trp Val Arg Gln Ala Pro Gly Gln Gly Leu
    50                  55                  60

Glu Trp Val Gly Ile Ile Asn Pro Ser Gly Gly Ile Thr Arg Tyr Ala
65                  70                  75                  80

Gln Lys Phe Gln Gly Arg Val Thr Leu Thr Arg Asp Thr Ser Thr Thr
                85                  90                  95

Thr Val Tyr Met Glu Leu Ser Ser Leu Arg Ser Glu Asp Thr Ala Val
            100                 105                 110

Tyr Tyr Cys Ala Arg Asp Arg Tyr Pro Val Leu Phe Ala Thr Asp Tyr
        115                 120                 125

Gly Met Asp Val Trp Gly Gln Gly Thr Thr Val Thr Val Ser Ser Ala
        130                 135                 140
```

```
Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

```
<210> SEQ ID NO 6
<211> LENGTH: 1419
<212> TYPE: DNA
<213> ORGANISM: Artificial Sequence
<220> FEATURE:
<223> OTHER INFORMATION: DMAb-30 Heavy Chain

<400> SEQUENCE: 6
atggactgga cctggagaat cctgttcctg gtggcagcag caacaggaac ccacgcacag      60
gtgcagctgg tgcagtccgg agcagaggtg acaaagccag gagccagcgt gaaggtgtcc     120
tgcaaggcct ctggctacac cttcaccaca tactatatgc actgggtgag gcaggcacct     180
```

-continued

```
ggacagggcc tggagtgggt gggcatcatc aacccaagcg gcggcatcac aagatacgcc      240
cagaagtttc agggaagggt gacactgacc cgcgacacca gcaccacaac cgtgtatatg      300
gagctgagct ccctgcgctc cgaggacaca gccgtgtact attgcgccag ggatagatac      360
cccgtgctgt tcgccaccga ctatggcatg gacgtgtggg gccagggcac aaccgtgaca      420
gtgtctagcg ccagcaccaa gggcccttcc gtgtttccac tggccccctc ctctaagtcc      480
acatctggcg gcaccgccgc cctgggatgt ctggtgaagg attatttccc agagcccgtg      540
accgtgtctt ggaacagcgg cgccctgaca tccggagtgc acacctttcc tgccgtgctg      600
cagagctccg gcctgtacag cctgtctagc gtggtcacag tgccatcctc tagcctgggc      660
acacagacct atatctgcaa cgtgaatcac aagccatcca ataccaaggt ggacaagaag      720
gtggagccca gtcttgtgta aagacacac acctgccctc cctgtcctgc accagagctg      780
ctgggcggcc caagcgtgtt cctgtttcca cccaagccta aggacaccct gatgatctct      840
aggacaccag aggtgacctg cgtggtggtg gacgtgagcc acgaggaccc cgaggtgaag      900
tttaactggt acgtggatgg cgtggaggtg cacaatgcca agaccaagcc aagggaggag      960
cagtacaatt ctacatatag agtggtgagc gtgctgaccg tgctgcacca ggactggctg     1020
aacggcaagg agtataagtg caaggtgtcc aataaggccc tgcccgcccc tatcgagaag     1080
acaatctcta aggcaaaggg acagcctcgg gagccacagg tgtacaccct gcctccatct     1140
cgcgacgagc tgacaaagaa ccaggtgagc ctgacctgtc tggtgaaggg cttctatccc     1200
agcgatatcg ccgtggagtg gggagtccaat ggccagcctg agaacaatta caagacaacc     1260
cctcccgtgc tggactccga tggctctttc tttctgtatt ccaagctgac agtggataag     1320
tctagatggc agcagggcaa cgtgtttagc tgttccgtga tgcacgaggc cctgcacaat     1380
cactacaccc agaagtctct gagcctgtcc cctggcaag                            1419
```

<210> SEQ ID NO 7
<211> LENGTH: 234
<212> TYPE: PRT
<213> ORGANISM: Artificial Sequence
<220> FEATURE:
<223> OTHER INFORMATION: DMAb-30 Light Chain

<400> SEQUENCE: 7

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Gly Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Ile Trp Pro Pro Gly Val Thr Phe Gly Gly Gly Thr Lys Val Glu Ile
        115                 120                 125

Lys Thr Val Ala Ala Pro Ser Val Phe Ile Phe Pro Pro Ser Asp Glu
    130                 135                 140
```

-continued

```
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 8
<211> LENGTH: 702
<212> TYPE: DNA
<213> ORGANISM: Artificial Sequence
<220> FEATURE:
<223> OTHER INFORMATION: DMAb-30 Light Chain

<400> SEQUENCE: 8
atggtgctgc agacccaggt gttcatcagc ctgctgctgt ggatctccgg cgcctacggc      60
gacatcgtga tgacccagtc cccagccaca ctgagcctgt cccctggaga gagggccacc     120
ctgtcttgca gagcctctca gagcgtgtcc ggctacctgg cctggtatca gcagaagcct     180
ggccaggccc caaggctgct gatctatgat gcatctaaca gggcaaccgg catcccagca     240
cgcttctctg gcagcggctc cggcacagac tttaccctga caatcagctc cctggagccc     300
gaggatttcg ccgtgtacta ttgccagcag agaagcatct ggccccctgg agtgaccttc     360
ggcggcggca caaggtgga gatcaagacc gtggccgccc ctagcgtgtt catctttcca     420
cccagcgacg agcagctgaa gtccggcaca gcctctgtgg tgtgcctgct gaacaatttc     480
tacccacggg aggccaaggt gcagtggaag gtggataacg ccctgcagtc tggcaatagc     540
caggagtccg tgaccgagca ggacaaggat tctacatata gcctgtctag caccctgaca     600
ctgagcaagg ccgactacga gaagcacaag gtgtatgcat gcgaggtgac ccaccagggc     660
ctgtcctctc ccgtgacaaa gtcctttaat cgcggcgagt gt                        702
```

```
<210> SEQ ID NO 9
<211> LENGTH: 468
<212> TYPE: PRT
<213> ORGANISM: Artificial Sequence
<220> FEATURE:
<223> OTHER INFORMATION: DMAb-34 Heavy Chain

<400> SEQUENCE: 9

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Ser Tyr Gly Phe Ser Trp Val Arg Gln Ala Pro Gly Gln Gly Leu
    50                  55                  60

Glu Trp Met Gly Trp Ile Ser Ala Tyr Asn Gly Tyr Thr Lys Tyr Ala
65                  70                  75                  80

Gln Lys Phe Gln Gly Arg Val Thr Met Thr Thr Asp Thr Ser Thr Arg
```

-continued

```
                85              90              95

Thr Ala Tyr Met Glu Leu Arg Ser Leu Arg Ser Asp Asp Ala Ala Val
            100             105             110

Tyr Tyr Cys Ala Arg Asp Leu Thr Pro Arg Asp Gly Met Asp Val Trp
            115             120             125

Gly Gln Gly Thr Thr Val Thr Val Ser Ser Ala Ser Thr Lys Gly Pro
    130             135             140

Ser Val Phe Pro Leu Ala Pro Ser Ser Lys Ser Thr Ser Gly Gly Thr
145             150             155             160

Ala Ala Leu Gly Cys Leu Val Lys Asp Tyr Phe Pro Glu Pro Val Thr
            165             170             175

Val Ser Trp Asn Ser Gly Ala Leu Thr Ser Gly Val His Thr Phe Pro
            180             185             190

Ala Val Leu Gln Ser Ser Gly Leu Tyr Ser Leu Ser Ser Val Val Thr
            195             200             205

Val Pro Ser Ser Ser Leu Gly Thr Gln Thr Tyr Ile Cys Asn Val Asn
    210             215             220

His Lys Pro Ser Asn Thr Lys Val Asp Lys Lys Val Glu Pro Lys Ser
225             230             235             240

Cys Asp Lys Thr His Thr Cys Pro Pro Cys Pro Ala Pro Glu Leu Leu
            245             250             255

Gly Gly Pro Ser Val Phe Leu Phe Pro Pro Lys Pro Lys Asp Thr Leu
            260             265             270

Met Ile Ser Arg Thr Pro Glu Val Thr Cys Val Val Val Asp Val Ser
            275             280             285

His Glu Asp Pro Glu Val Lys Phe Asn Trp Tyr Val Asp Gly Val Glu
    290             295             300

Val His Asn Ala Lys Thr Lys Pro Arg Glu Glu Gln Tyr Asn Ser Thr
305             310             315             320

Tyr Arg Val Val Ser Val Leu Thr Val Leu His Gln Asp Trp Leu Asn
            325             330             335

Gly Lys Glu Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Lys Asn Gln Val
    370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
            405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
    450             455             460

Ser Pro Gly Lys
465
```

<210> SEQ ID NO 10
<211> LENGTH: 1431
<212> TYPE: DNA
<213> ORGANISM: Artificial Sequence -continued

```
<220> FEATURE:
<223> OTHER INFORMATION: DMAb-34 Heavy Chain

<400> SEQUENCE: 10
ggatccgccg ccaccatgga ctggacatgg agaatcctgt tcctggtggc agcagcaacc        60
ggaacacacg cacaggtgca gctggtgcag tccggagcag aggtgaagaa gccaggagcc       120
tctgtgaagg tgagctgcaa ggcctccggc tataccttca gctcctacgg cttttcttgg       180
gtgcgccagg cacctggaca gggcctggag tggatgggct ggatcagcgc ctacaacggc       240
tatacaaagt acgcccagaa gttccagggc cgggtgacca tgaccacaga caccagcaca       300
cgcaccgcct atatggagct gaggagcctg agaagcgacg atgccgccgt gtactattgc       360
gcccgggatc tgacccctcg cgacggaatg gacgtgtggg gacagggaac cacagtgaca       420
gtgtctagcg cctctaccaa gggcccaagc gtgtttccac tggcccccc ctctaagtcc        480 acatctggcg gcaccgccgc cctgggatgt ctggtgaagg attacttccc agagcccgtg       540
accgtgtcct ggaactctgg cgccctgaca agcggcgtgc acacctttcc agccgtgctg       600
cagagctccg gcctgtattc cctgtctagc gtggtgacag tgccctcctc tagcctgggc       660
acacagacct acatctgcaa cgtgaatcac aagccaagca ataccaaggt ggacaagaag       720
gtggagccca gtcctgtga taagacacac acctgccctc cctgtcctgc accagagctg        780
ctgggcggcc catccgtgtt cctgtttcca cccaagccta aggacacact gatgatctct       840
aggacacccg aggtgacctg cgtggtggtg gacgtgagcc acgaggaccc cgaggtgaag       900
tttaactggt acgtggatgg cgtggaggtg cacaatgcca agaccaagcc aagggaggag       960
cagtataatt ccacatacag agtggtgtct gtgctgaccg tgctgcacca ggactggctg      1020
aacggcaagg agtacaagtg caaggtgtcc aataaggccc tgcccgcccc tatcgagaag      1080
acaatctcta aggccaaggg ccagcctagg gagccacagg tgtatacct gcctccatcc       1140 agagacgagc tgacaaagaa ccaggtgtct ctgacctgtc tggtgaaggg cttctaccct      1200
tctgatatcg ccgtggagtg ggagagcaat ggccagccag agaacaatta taagaccaca      1260
ccccctgtgc tggacagcga tggctccttc tttctgtaca gcaagctgac agtggataag      1320
tccagatggc agcagggcaa cgtgtttagc tgttccgtga tgcacgaggc cctgcacaat      1380
cactacaccc agaagtctct gagcctgtcc cctggcaagt gataactcga g              1431

<210> SEQ ID NO 11
<211> LENGTH: 238
<212> TYPE: PRT
<213> ORGANISM: Artificial Sequence
<220> FEATURE:
<223> OTHER INFORMATION: DMAb-34 Light Chain

<400> SEQUENCE: 11

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu His Ser Asn Gly Tyr Asn Tyr Leu Asp Trp Tyr Leu Gln Lys
    50                  55                  60

Pro Gly Gln Pro Pro Gln Val Leu Ile Ser Leu Gly Ser Asn Arg Ala
65                  70                  75                  80

Ser Gly Val Pro Asp Arg Phe Ser Gly Ser Gly Ser Gly Thr Asp Phe
```

```
                    85              90              95
Thr Leu Lys Ile Ser Arg Val Glu Ala Glu Asp Val Gly Val Tyr Tyr
            100             105             110
Cys Met Gln Ala Leu Gln Thr Pro Arg Thr Phe Gly Gln Gly Thr Lys
            115             120             125
Val Glu Ile Lys Thr Val Ala Ala Pro Ser Val Phe Ile Phe Pro Pro
        130             135             140
Ser Asp Glu Gln Leu Lys Ser Gly Thr Ala Ser Val Val Cys Leu Leu
145             150             155             160
Asn Asn Phe Tyr Pro Arg Glu Ala Lys Val Gln Trp Lys Val Asp Asn
                165             170             175
Ala Leu Gln Ser Gly Asn Ser Gln Glu Ser Val Thr Glu Gln Asp Ser
            180             185             190
Lys Asp Ser Thr Tyr Ser Leu Ser Ser Thr Leu Thr Leu Ser Lys Ala
            195             200             205
Asp Tyr Glu Lys His Lys Val Tyr Ala Cys Glu Val Thr His Gln Gly
        210             215             220
Leu Ser Ser Pro Val Thr Lys Ser Phe Asn Arg Gly Glu Cys
225             230             235
```

<210> SEQ ID NO 12
<211> LENGTH: 741
<212> TYPE: DNA
<213> ORGANISM: Artificial Sequence
<220> FEATURE:
<223> OTHER INFORMATION: DMAb-34 Light Chain

<400> SEQUENCE: 12

```
ggatccgccg ccaccatggt gctgcagacc caggtgttca tctccctgct gctgtggatc      60
tctggcgcct acggcgacat cgtgctgacc cagtctcctc tgagcctgcc tgtgacacca     120
ggagagccag caagcatctc ctgcaggagc tcccagagcc tgctgcactc caacggctac     180
aattatctgg attggtatct gcagaagcca ggacagcccc ctcaggtgct gatctccctg     240
ggctctaaca gggcctctgg cgtgcctgac agattctctg gcagcggctc cggaaccgac     300
ttcaccctga agatcagccg ggtggaggca gaggacgtgg gcgtgtacta ttgcatgcag     360
gccctgcaga cccctcgcac attcggccag ggcaccaagg tggagatcaa gacagtggcc     420
gccccaagcg tgttcatctt ccaccctcc gacgagcagc tgaagtctgg cacagccagc     480
gtggtgtgcc tgctgaacaa cttctaccca agggaggcca aggtgcagtg gaaggtggat     540
aacgccctgc agagcggcaa ttcccaggag tctgtgaccg agcaggacag caaggattcc     600
acatattctc tgtctagcac cctgacactg tccaaggccg attacgagaa gcacaaggtg     660
tatgcatgcg aggtgaccca ccagggcctg tcctctcccg tgacaaagag ctttaatcgg     720
ggcgagtgtt gataactcga g                                              741
```

<210> SEQ ID NO 13
<211> LENGTH: 739
<212> TYPE: PRT
<213> ORGANISM: Artificial Sequence
<220> FEATURE:
<223> OTHER INFORMATION: DMAb-11

<400> SEQUENCE: 13

```
Met Asp Trp Thr Trp Arg Ile Leu Phe Leu Val Ala Ala Ala Thr Gly
1               5               10              15
Thr His Ala Glu Val Gln Leu Val Glu Ser Gly Gly Gly Leu Ile Gln
```

-continued

```
                 20                25                30

Pro Gly Gly Ser Leu Arg Leu Ser Cys Ala Ala Ser Gly Phe Ala Val
             35                40                45

Arg Ser Asn Tyr Leu Ser Trp Val Arg Gln Ala Pro Gly Lys Gly Leu
         50                55                60

Glu Trp Val Ser Leu Ile Tyr Ser Gly Gly Leu Thr Ala Tyr Ala Asp
65                70                75                80

Ser Val Glu Gly Arg Phe Thr Ile Ser Arg Asp Asn Ser Lys Asn Thr
                 85                90                95

Leu Tyr Leu Gln Met Asn Ser Leu Arg Val Glu Asp Thr Ala Leu Tyr
                 100               105               110

Tyr Cys Ala Arg Val Ala Ser Ser Ala Gly Thr Phe Tyr Tyr Gly Met
             115               120               125

Asp Val Trp Gly Gln Gly Thr Thr Val Thr Val Ser Ser Ala Ser Thr
             130               135               140

Lys Gly Pro Ser Val Phe Pro Leu Ala Pro Ser Ser Lys Ser Thr Ser
145               150               155               160

Gly Gly Thr Ala Ala Leu Gly Cys Leu Val Lys Asp Tyr Phe Pro Glu
                 165               170               175

Pro Val Thr Val Ser Trp Asn Ser Gly Ala Leu Thr Ser Gly Val His
             180               185               190

Thr Phe Pro Ala Val Leu Gln Ser Ser Gly Leu Tyr Ser Leu Ser Ser
             195               200               205

Val Val Thr Val Pro Ser Ser Ser Leu Gly Thr Gln Thr Tyr Ile Cys
         210               215               220

Asn Val Asn His Lys Pro Ser Asn Thr Lys Val Asp Lys Lys Val Glu
225               230               235               240

Pro Lys Ser Cys Asp Lys Thr His Thr Cys Pro Pro Cys Pro Ala Pro
             245               250               255

Glu Leu Leu Gly Gly Pro Ser Val Phe Leu Phe Pro Pro Lys Pro Lys
             260               265               270

Asp Thr Leu Met Ile Ser Arg Thr Pro Glu Val Thr Cys Val Val Val
             275               280               285

Asp Val Ser His Glu Asp Pro Glu Val Lys Phe Asn Trp Tyr Val Asp
         290               295               300

Gly Val Glu Val His Asn Ala Lys Thr Lys Pro Arg Glu Glu Gln Tyr
305               310               315               320

Asn Ser Thr Tyr Arg Val Val Ser Val Leu Thr Val Leu His Gln Asp
                 325               330               335

Trp Leu Asn Gly Lys Glu Tyr Lys Cys Lys Val Ser Asn Lys Ala Leu
             340               345               350

Pro Ala Pro Ile Glu Lys Thr Ile Ser Lys Ala Lys Gly Gln Pro Arg
             355               360               365

Glu Pro Gln Val Tyr Thr Leu Pro Pro Ser Arg Asp Glu Leu Thr Lys
         370               375               380

Asn Gln Val Ser Leu Thr Cys Leu Val Lys Gly Phe Tyr Pro Ser Asp
385               390               395               400

Ile Ala Val Glu Trp Glu Ser Asn Gly Gln Pro Glu Asn Asn Tyr Lys
             405               410               415

Thr Thr Pro Pro Val Leu Asp Ser Asp Gly Ser Phe Phe Leu Tyr Ser
             420               425               430

Lys Leu Thr Val Asp Lys Ser Arg Trp Gln Gln Gly Asn Val Phe Ser
             435               440               445
```

-continued

```
Cys Ser Val Met His Glu Ala Leu His Asn His Tyr Thr Gln Lys Ser
    450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Asp Ile Val Met Thr Gln Ser Pro
        515                 520                 525

Arg Ser Leu Ser Val Thr Pro Gly Glu Pro Ala Ser Ile Ser Cys Arg
    530                 535                 540

Ser Ser Gln Ser Leu Leu His Arg Asn Gly Tyr Asn Tyr Leu Asp Trp
545                 550                 555                 560

Tyr Leu Gln Lys Pro Gly Gln Ser Pro Gln Leu Leu Ile Tyr Leu Gly
                565                 570                 575

Ser Asn Arg Ala Ser Gly Val Pro Asp Arg Phe Ser Gly Ser Gly Ser
            580                 585                 590

Gly Thr Asp Phe Thr Leu Lys Ile Ser Arg Val Glu Ala Glu Asp Val
        595                 600                 605

Gly Val Tyr Tyr Cys Met Gln Ala Leu Gln Thr Pro Ser Trp Thr Phe
    610                 615                 620

Gly Gln Gly Thr Lys Val Glu Ile Lys Thr Val Ala Ala Pro Ser Val
625                 630                 635                 640

Phe Ile Phe Pro Pro Ser Asp Glu Gln Leu Lys Ser Gly Thr Ala Ser
                645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
        675                 680                 685

Thr Glu Gln Asp Ser Lys Asp Ser Thr Tyr Ser Leu Ser Ser Thr Leu
    690                 695                 700

Thr Leu Ser Lys Ala Asp Tyr Glu Lys His Lys Val Tyr Ala Cys Glu
705                 710                 715                 720

Val Thr His Gln Gly Leu Ser Ser Pro Val Thr Lys Ser Phe Asn Arg
                725                 730                 735

Gly Glu Cys
```

```
<210> SEQ ID NO 14
<211> LENGTH: 2244
<212> TYPE: DNA
<213> ORGANISM: Artificial Sequence
<220> FEATURE:
<223> OTHER INFORMATION: DMAb-11

<400> SEQUENCE: 14
ggatccgccg ccaccatgga ctggacctgg agaatcctgt tcctggtggc agcagcaacc      60
ggaacacacg cagaggtgca gctggtggag agcggcggcg gcctgatcca gccaggcggc     120
agcctgaggc tgtcctgcgc agcatctgga tttgccgtga ggagcaacta cctgtcctgg     180
gtgagacagg caccaggcaa gggactggag tgggtgtctc tgatctacag cggcggcctg     240
accgcatatg cagacagcgt ggagggcagg ttcaccatct ccagagataa ctctaagaat     300
acactgtatc tgcagatgaa cttcctgcgg gtggaggaca ccgccctgta ctattgcgcc     360
```

-continued

```
cgcgtggcca gctccgccgg cacattctac tatggcatgg acgtgtgggg ccagggcacc      420
acagtgaccg tgtctagcgc ctccacaaag ggaccaagcg tgttcccact ggcaccttcc      480
tctaagtcca cctctggcgg cacagccgcc ctgggctgtc tggtgaagga ttacttccct      540
gagccagtga ccgtgtcttg gaacagcggc gccctgacca cgggagtgca cacatttcct      600
gccgtgctgc agagctccgg cctgtactcc ctgtctagcg tggtgaccgt gccatcctct      660
agcctgggca cccagacata tatctgcaac gtgaatcaca gcctagcaa tacaaaggtg      720 gacaagaagg tggagccaaa gtcctgtgat aagacccaca catgccctcc ctgtccagca      780
cctgagctgc tgggcggccc aagcgtgttc ctgtttccac ccaagcccaa ggacacactg      840
atgatctcta ggaccccaga ggtgacatgc gtggtggtgg acgtgagcca cgaggacccc      900
gaggtgaagt ttaactggta cgtggatggc gtggaggtgc acaatgccaa gaccaagcca      960
agggaggagc agtacaacag cacctataga gtggtgtccg tgctgacagt gctgcaccag     1020
gactggctga acggcaagga gtataagtgc aaggtgtcca ataaggccct gccagccccc     1080
atcgagaaga ccatctctaa ggcaaaggga cagccaaggg agccacaggt gtacacactg     1140
cctccatcca gagacgagct gaccaagaac caggtgtctc tgacatgtct ggtgaagggc     1200
ttctatccct ctgatatcgc cgtggagtgg gagagcaatg gccagcctga gaacaattac     1260
aagaccacac cccctgtgct ggactccgat ggctctttct ttctgtattc caagctgacc     1320
gtggataagt ctcggtggca gcagggcaac gtgtttagct gctccgtgat gcacgaggcc     1380
ctgcacaatc actacaccca gaagtctctg agcctgtccc ctggcaagag gggaaggaag     1440
aggagatctg gcagcggcgc cacaaacttc agcctgctga agcaggcagg cgacgtggag     1500
gagaatcctg gaccaatggt gctgcagacc caggtgttta tctctctgct gctgtggatc     1560
agcggcgcct acggcgatat cgtgatgacc cagtcccctc gctccctgtc tgtgacacct     1620
ggcgagccag ccagcatctc ctgtcggtcc tctcagtctc tgctgcaccg caacggctac     1680
aattatctgg actggtacct gcagaagccc ggccagtccc ctcagctgct gatctatctg     1740
ggcagcaaca gggcatccgg agtgccagac cgcttctctg gcagcggctc cggaaccgac     1800
ttcaccctga gatcagcag ggtggaggcc gaggatgtgg gcgtgtacta ttgcatgcag     1860
gccctgcaga ccccctcctg gacattcggc cagggcacca aggtggagat caagacagtg     1920 gccgcccta gcgtgttcat ctttccaccc tccgacgagc agctgaagtc tggcaccgcc     1980
agcgtggtgt gcctgctgaa caacttctac cccagagagg ccaaggtgca gtggaaggtg     2040
gataacgccc tgcagagcgg caattcccag gagtctgtga ccgagcagga cagcaaggat     2100
tccacatatt ctctgagctc caccctgaca ctgagcaagg ccgactacga gaagcacaag     2160
gtgtatgcct gcgaggtgac ccaccagggc ctgtctagcc ctgtgacaaa gtccttcaac     2220
agaggcgagt gttgataact cgag                                            2244
```

NUCLEIC ACID ANTIBODY CONSTRUCTS FOR USE AGAINST EBOLA VIRUS

CROSS-REFERENCE TO RELATED APPLICATIONS

This application is entitled to priority to U.S. Provisional Application No. 62/624,308, filed Jan. 31, 2018, which is incorporated by reference herein in its entirety.

TECHNICAL FIELD

Cross-Reference to Related Applications

This application is a U.S. national phase application filed under 35 U.S.C. § 371 claiming priority to International Patent Application No. PCT/US19/15984, filed Jan. 31, 2019, which is entitled to priority under 35 U.S.C. § 119(e) to U.S. Provisional Application No. 62/624,308, filed Jan. 31, 2018, the contents of each of which are incorporated by reference herein in their entireties.

BACKGROUND

In the 2013-2016 Ebola virus disease (EVD) epidemic in West Africa, an anti-glycoprotein (GP) monoclonal antibody (mAb) cocktail, ZMapp, was associated with favorable recovery in human patients. Since then, several mAb clones with greater potency than the ZMapp clones have been isolated from human EVD survivors. Monoclonal antibodies (mAbs) targeting the Ebola virus glycoprotein (GP) represent an important treatment approach against Ebola virus disease (EVD). It has been shown that individual mAbs and mAb cocktails can successfully protect small animals and non-human primates against lethal Ebola virus infection. MAb-based therapy against EVD is further supported by favorable recovery in confirmed human EVD cases that received the anti-GP mAb cocktail, ZMapp. However, the dramatic cost, slow development, and requirement for several high-dose administrations (mg/kg) represent a significant challenge for protein mAb delivery, especially during a possible outbreak.

Thus, there is need in the art for improved therapeutics that prevent and/or treat Ebola virus infection. The current invention satisfies this need.

SUMMARY

The present invention is directed to a nucleic acid molecule encoding one or more synthetic antibodies, wherein the nucleic acid molecule comprises at least one selected from the group consisting of a) a nucleotide sequence encoding an anti-Ebola virus glycoprotein (GP) synthetic antibody; and b) a nucleotide sequence encoding a fragment of an anti-Ebola virus glycoprotein (GP) synthetic antibody.

In one embodiment, the nucleic acid molecule comprises a nucleotide sequence encoding a cleavage domain.

In one embodiment, the nucleic acid molecule comprises a nucleotide sequence encoding one or more of a variable heavy chain region and a variable light chain region of an anti-Ebola virus GP antibody.

In one embodiment, the nucleic acid molecule encodes one or more synthetic bispecific antibodies. A bispecific antibody molecule according to the invention may have two binding sites of any desired specificity. In some embodiments one of the binding sites is capable of binding an Ebola virus antigen. In some embodiment, one of the binding sites is capable of binding a cell surface marker on an immune cell.

In one embodiment, the nucleic acid molecule comprises a nucleotide sequence encoding one or more sequences as set forth in SEQ ID NO:1, SEQ ID NO:3, SEQ ID NO:5, SEQ ID NO:7, SEQ ID NO:9, SEQ ID NO:11, and SEQ ID NO:13, or a variant thereof or a fragment thereof.

In one embodiment, the nucleic acid molecule comprises a nucleotide sequence encoding a variable heavy chain region and a variable light chain region of an anti-Ebola virus GP antibody. In one embodiment, the nucleic acid molecule comprises a nucleotide sequence comprising a sequence selected from the group comprising SEQ ID NO:2, SEQ ID NO:4, SEQ ID NO:6, SEQ ID NO:8, SEQ ID NO:10, SEQ ID NO:12, and SEQ ID NO:14, or a variant thereof or a fragment thereof.

In one embodiment, the nucleic acid molecule comprises a nucleotide sequence encoding a polypeptide comprising a variable heavy chain region; an IRES element; and a variable light chain region. In one embodiment, the IRES element is one of a viral IRES or an eukaryotic IRES.

In one embodiment, the nucleic acid molecule comprises a nucleotide sequence having at least about 95% identity over an entire length of the nucleic acid sequence to a nucleic acid encoding a sequence selected from the group consisting of SEQ ID NO:1, SEQ ID NO:3, SEQ ID NO:5, SEQ ID NO:7, SEQ ID NO:9, SEQ ID NO:11, and SEQ ID NO:13, or a variant thereof or a fragment thereof.

In one embodiment, the nucleic acid molecule comprises a nucleotide sequence encoding a sequence selected from the group consisting of SEQ ID NO:1, SEQ ID NO:3, SEQ ID NO:5, SEQ ID NO:7, SEQ ID NO:9, SEQ ID NO:11, and SEQ ID NO:13, or a variant thereof or a fragment thereof.

In one embodiment, the nucleic acid molecule comprises a nucleotide sequence having at least about 95% identity over an entire length of the nucleic acid sequence to a nucleic acid sequence selected from the group consisting of SEQ ID NO:2, SEQ ID NO:4, SEQ ID NO:6, SEQ ID NO:8, SEQ ID NO:10, SEQ ID NO:12, and SEQ ID NO:14.

In one embodiment, the nucleic acid molecule comprises a nucleotide sequence selected from the group consisting of SEQ ID NO:2, SEQ ID NO:4, SEQ ID NO:6, SEQ ID NO:8, SEQ ID NO:10, SEQ ID NO:12, and SEQ ID NO:14, or a variant thereof or a fragment thereof.

In one embodiment, the nucleic acid molecule comprises a RNA sequence transcribed from a DNA sequence described herein. For example, in one embodiment, the nucleic acid molecule comprises a RNA sequence transcribed by the DNA sequence of SEQ ID NOs: SEQ ID NO:1, SEQ ID NO:3, SEQ ID NO:5, SEQ ID NO:7, SEQ ID NO:9, SEQ ID NO:11, and SEQ ID NO:13, or a variant thereof or a fragment thereof. In another embodiment, the nucleic acid molecule comprises an RNA sequence transcribed by a DNA sequence encoding the polypeptide sequence of SEQ ID NOs: SEQ ID NO:2, SEQ ID NO:4, SEQ ID NO:6, SEQ ID NO:8, SEQ ID NO:10, SEQ ID NO:12, and SEQ ID NO:14, or a variant thereof or a fragment thereof.

In one embodiment, the nucleotide sequence encodes a leader sequence. In one embodiment, the nucleic acid molecule comprises an expression vector.

The invention further provides a composition comprising any of the nucleic acid molecules described herein. In one embodiment, the composition comprises at least one of the nucleic acid molecules described herein. In one embodiment, the composition comprises at least two of the nucleic acid molecules described herein. In one embodiment, the composition comprises at least three of the nucleic acid molecules described herein.

In one embodiment, the composition comprises a pharmaceutically acceptable excipient.

The invention further relates to a method of preventing or treating a disease in a subject, the method comprising administering to the subject a nucleic acid molecule or a composition as described herein.

In one embodiment, the disease is an Ebola virus infection.

In one embodiment, the method further comprises administering an antibiotic agent to the subject. In one embodiment, an antibiotic is administered less than 10 days after administration of the nucleic acid molecule or composition.

In one embodiment, the method further comprises administering an antibiotic agent to the subject. In one embodiment an antibiotic is administered less than 10 days after administration of the nucleic acid molecule or composition.

In one embodiment, the invention provides novel sequences for use for producing monoclonal antibodies in mammalian cells or for delivery in DNA or RNA vectors including bacterial, yeast, as well as viral vectors.

DETAILED DESCRIPTION

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

A sequence listing provided herewith contains a list of 14 sequences including the following:

SEQ ID NO:1 is the amino acid sequence of DMAb-11 heavy chain.

SEQ ID NO:2 is the nucleotide sequence of DMAb-11 heavy chain.

SEQ ID NO:3 is the amino acid sequence of DMAb-11 light chain.

SEQ ID NO:4 is the nucleotide sequence of DMAb-11 light chain.

SEQ ID NO:5 is the amino acid sequence of DMAb-30 heavy chain.

SEQ ID NO:6 is the nucleotide sequence of DMAb-30 heavy chain.

SEQ ID NO:7 is the amino acid sequence of DMAb-30 light chain.

SEQ ID NO:8 is the nucleotide sequence of DMAb-30 light chain.

SEQ ID NO:9 is the amino acid sequence of DMAb-34 heavy chain.

SEQ ID NO:10 is the nucleotide sequence of DMAb-34 heavy chain.

SEQ ID NO:11 is the amino acid sequence of DMAb-34 light chain.

SEQ ID NO:12 is the nucleotide sequence of DMAb-34 light chain.

SEQ ID NO:13 is the amino acid sequence of DMAb-11.

SEQ ID NO:14 is the nucleotide sequence of DMAb-11.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-Ebola Glycoprotein (anti-Ebola GP) antibody.

In one embodiment, the nucleotide sequence encoding an anti-Ebola GP antibody comprises one or more codon optimized nucleic acid sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, and SEQ ID NO:13, or a fragment thereof.

In one embodiment, the nucleotide sequence encoding an anti-Ebola GP antibody comprises one or more RNA sequence transcribed from one or more DNA sequences encoding an amino acid sequence at least 95% homologous to an amino acid sequence as set forth in SEQ ID NO:1, SEQ ID NO:3, SEQ ID NO:5, SEQ ID NO:7, SEQ ID NO:9, SEQ ID NO:11, and SEQ ID NO:13, or a fragment thereof.

In one embodiment, the nucleotide sequence encoding an anti-Ebola GP antibody comprises one or more codon optimized nucleic acid sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, and SEQ ID NO:14, or a fragment thereof.

In one embodiment, the nucleotide sequence encoding an anti-Ebola GP antibody comprises one or more RNA sequence transcribed from one or more DNA sequences at least 95% homologous to a nucleic acid sequence as set forth in SEQ ID NO:2, SEQ ID NO:4, SEQ ID NO:6, SEQ ID NO:8, SEQ ID NO:10, SEQ ID NO:12, and SEQ ID NO:14, or a fragment thereof.

The composition of the invention can treat, prevent and/or protect against any disease, disorder, or condition associated with Ebola infection. In certain embodiments, the composition can treat, prevent, and or/protect against viral infection. In certain embodiments, the composition can treat, prevent, and or/protect against condition associated with Ebola infection.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. RECOMBINANT NUCLEIC ACID SEQUENCE

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human ($\beta$-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(12) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide. For example, in one embodiment, the first recombinant nucleic acid sequence encodes a heavy chain polypeptide having an amino acid sequence at least 95% homologous to SEQ ID NO: 1, SEQ ID NO: 5, or SEQ ID NO: 9. In one embodiment, the first recombinant nucleic acid sequence comprises a nucleic acid sequence at least 95% homologous to SEQ ID NO: 2, SEQ ID NO: 6, or SEQ ID NO:10. In one embodiment, the second recombinant nucleic acid sequence encodes a light chain polypeptide having an amino acid sequence at least 95% homologous to SEQ ID NO: 3, SEQ ID NO: 7, or SEQ ID NO: 1. In one embodiment, the second recombinant nucleic acid sequence comprises a nucleic acid sequence at least 95% homologous to SEQ ID NO: 4, SEQ ID NO: 8, or SEQ ID NO:12.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(13) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CHL and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(14) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(15) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, CA), which may be used for protein production in *Escheri-*

*chia coli* (*E. coli*). The plasmid may also be pYES2 (Invitrogen, San Diego, CA), which may be used for protein production in Saccharomyces cerevisiae strains of yeast. The plasmid may also be of the MAXBAC™ complete baculovirus expression system (Invitrogen, San Diego, CA), which may be used for protein production in insect cells. The plasmid may also be pcDNAI or pcDNA3 (Invitrogen, San Diego, CA), which may be used for protein production in mammalian cells such as Chinese hamster ovary (CHO) cells.

(16) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NOs: 2, 4, 6, 8, 10, 12, or 14. In another embodiment, the nucleotide sequence comprises an RNA sequence transcribed by a DNA sequence encoding a polypeptide sequence of SEQ ID NOs:1, 3, 5, 7, 9, 11, or 13, or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(17) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(18) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585, 362.

(19) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

In one embodiment, the antibody binds an ebolavirus antigen. In one embodiment, the antibody binds an ebolavirus glycoprotein. In one embodiment, the antibody binds at least one an epitope of an ebolavirus glycoprotein. For example, in one embodiment, the antibody binds ebolavirus glycoprotein epitope comprising the reside W531, I527, or both.

The antibody may be modified to reduce or prevent antibody-dependent enhancement (ADE) of disease associated with the antigen as described in more detail below.

Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments one of the binding sites is capable of binding a tumor associated antigen. In some embodiments, the binding site included in the Fab fragment is a binding site specific for a Ebolavirus antigen. In some embodiments, the binding site included in the single chain Fv fragment is a binding site specific for a Ebolavirus antigen such as a Ebolavirus glycoprotein antigen.

In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing. alpha.- and .beta.-chains, in some embodiments it encompasses .gamma.-chains and .delta.-chains (supra). Accordingly, in some embodiments the TCR is TCR (alpha/beta) and in some embodiments it is TCR (gamma/delta). The T cell receptor forms a complex with the CD3 T-Cell co-receptor. CD3 is a protein complex and is composed of four distinct chains. In mammals, the complex contains a CD3γ chain, a CD36 chain, and two CD3E chains. These chains associate with a molecule known as the T cell receptor (TCR) and the ζ-chain to generate an activation signal in T lymphocytes. Hence, in some embodiments a T-cell specific receptor is the CD3 T-Cell co-receptor. In some embodiments, a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments, the first binding site of the antibody molecule binds a Ebolavirus antigen and the second binding site binds a T cell specific receptor molecule and/or a natural killer (NK) cell specific receptor molecule.

In some embodiments, the first binding site of the antibody molecule binds one of Ebolavirus GP glycan cap, Ebolavirus GP fusion loop, or Ebolavirus GP chalice base, and the second binding site binds a T cell specific receptor molecule and/or a natural killer (NK) cell specific receptor molecule. In some embodiments, the first binding site of the antibody molecule binds a Ebolavirus antigen and the second binding site binds one of CD3, the T cell receptor (TCR), CD28, CD16, NKG2D, Ox40, 4-1BB, CD2, CD5 and CD95.

In some embodiments, the first binding site of the antibody molecule binds a T cell specific receptor molecule and/or a natural killer (NK) cell specific receptor molecule and the second binding site binds an Ebolavirus antigen. In some embodiments, the first binding site of the antibody binds a T cell specific receptor molecule and/or a natural killer (NK) cell specific receptor molecule and the second binding site binds one of Ebolavirus GP glycan cap, Ebolavirus GP fusion loop, or Ebolavirus GP chalice base. In some embodiments, the first binding site of the antibody binds one of CD3, the T cell receptor (TCR), CD28, CD16, NKG2D, Ox40, 4-1BB, CD2, CD5 and CD95, and the second binding site binds an Ebolavirus antigen.

Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve $Fc\gamma RIIIa$ binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to $Fc\gamma R1a$. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to $Fc\gamma R1a$, and thus, the modified antibody does not enhance or cause ADE of disease associated with the antigen, but still neutralizes the antigen.

5. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a virus. The antigen can be associated with viral infection. In one embodiment, the antigen can be associated with Ebola infection. In one embodiment, the antigen can be an Ebola glycoprotein.

In one embodiment, the antigen can be a fragment of an Ebola glycoprotein. For example, in one embodiment, the antigen is a fragment of an Ebola glycoprotein, wherein the fragment comprises the amino acid Trp531. In one embodiment, the antigen is a fragment of an Ebola glycoprotein, wherein the fragment comprises the amino acid Ile527. In one embodiment, the antigen is a fragment of an Ebola glycoprotein, wherein the fragment comprises the amino acids Trp531 and Ile527.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Viral Antigens

The viral antigen can be a viral antigen or fragment or variant thereof. The virus can be a disease causing virus. The virus can be the Ebola virus.

The antigen may be an Ebola viral antigen, or fragment thereof, or variant thereof. The Ebola antigen can be from a factor that allows the virus to replicate, infect or survive. Factors that allow an Ebola virus to replicate or survive include, but are not limited to structural proteins and non-structural proteins. Such a protein can be an envelope protein or a glycoprotein.

In one embodiment, an envelope protein is Ebola GP.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. Patent Application, Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. METHOD OF TREATMENT

Also provided herein is a method of treating, protecting against, and/or preventing disease in a subject in need thereof by generating the synthetic antibody in the subject. The method can include administering the composition to the subject. In one embodiment, the method can include administering a composition comprising at least one, at least two or at least 3 nucleic acids described herein. Administration of the composition to the subject can be done using the method of delivery described above.

In certain embodiments, the invention provides a method of treating protecting against, and/or preventing an Ebola Virus infection. In one embodiment, the method treats, protects against, and/or prevents a disease associated with Ebola Virus.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. USE IN COMBINATION WITH ANTIBIOTICS

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

The present invention has multiple aspects, illustrated by the following non-limiting examples.

12. GENERATION OF SYNTHETIC ANTIBODIES IN VITRO AND EX VIVO

In one embodiment, the synthetic antibody is generated in vitro or ex vivo. For example, in one embodiment, a nucleic acid encoding a synthetic antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

13. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

The studies presented herein demonstrate the generation of functional anti-Ebola "DNA monoclonal antibodies" (DMAb) via intramuscular electroporation of plasmid DNA.

The engineering of synthetic plasmid DNA expression cassette-delivered monoclonal antibodies (DMAbs) is described herein as a strategy for in vivo administration of potent mAb clones that frequently require high-dose administrations to maintain protective serum trough levels or have properties incompatible with bioprocess manufacturing. The DMAb platform facilitates direct in vivo transfection of muscle cells to produce and secrete into the blood mAb at biologically relevant levels. More than 30 human IgG1 anti-GP DMAbs were engineered from clones isolated from human EVD survivors and targeting different regions of the GP glycan cap, fusion loop, chalice base, HR2 region, or MPER region. Anti-GP DMAbs, administered by intramuscular injection followed by CELLECTRA adaptive constant current electroporation, were detectable in BALB/c mice for >120 days and share similar binding, neutralization, and epitope mapping properties to their protein IgG counterparts.

BALB/c mice (n=10/group) were administered DMAb-11, DMAb-30, or DMAb-34 and monitored for DMAb expression in serum. Mice were then challenged on day 28 following administration with a highly lethal 1000LD50 dose of mouse-adapted Ebola virus (strain Mayinga). 100% protection from both mortality and morbidity as observed following DMAb administration. A new combination of DMAb-11, DMAb-30, and DMAb-34 was co-delivered to BALB/c mice (n=10/group) as a DMAb-cocktail designed to evade potential Ebola virus escape mutants. The DMAb-11-30-34 cocktail was 100% protective at lower doses of the individual DMAbs. In a separate experiment, DMAb-11 was administered to BALB/c mice Day 8 before lethal challenge, observing 80% protection. This study supports the efficiency of DMAb delivery as an intervention for highly pathogenic hemorrhagic fever viruses and potential of a DMAb-cocktail approach. These studies demonstrate the importance of in vivo DMAb delivery as a novel approach for preventing deadly emerging infectious diseases including Ebola virus disease (EVD), and has implications for prevention and therapy of a range of infectious diseases as well as cancers.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

---

55

What is claimed is:

1. A composition comprising a first, a second, a third, a fourth, a fifth, and a sixth nucleotide sequence, wherein the first nucleotide sequence encodes SEQ ID NO: 1;

wherein the second nucleotide sequence encodes SEQ ID NO: 3;

wherein the third nucleotide sequence encodes SEQ ID NO: 5;

wherein the fourth nucleotide sequence encodes SEQ ID NO: 7;

wherein the fifth nucleotide sequence encodes SEQ ID NO: 9; and wherein the sixth nucleotide sequence encodes SEQ ID NO: 11.

2. The composition of claim 1, wherein the composition further comprises at least one nucleotide sequence encoding a protease cleavage site.

3. The composition of claim 1, wherein the first nucleotide sequence comprises a nucleotide sequence having at least 99% identity to SEQ ID NO:2;

wherein the second nucleotide sequence comprises a nucleotide sequence having at least 99% identity to SEQ ID NO:4;

wherein the third nucleotide sequence comprises a nucleotide sequence having at least 99% identity to SEQ ID NO:6;

wherein the fourth nucleotide sequence comprises a nucleotide sequence having at least 99% identity to SEQ ID NO:8;

wherein the fifth nucleotide sequence comprises a nucleotide sequence having at least 99% identity to SEQ ID NO:10; and wherein the sixth nucleotide sequence comprises a nucleotide sequence having at least 99% identity to SEQ ID NO:12.

4. The composition of claim 3, wherein the first nucleotide sequence comprises SEQ ID NO:2;

wherein the second nucleotide sequence comprises SEQ ID NO:4;

wherein the third nucleotide sequence comprises SEQ ID NO:6;

wherein the fourth nucleotide sequence comprises SEQ ID NO:8;

wherein the fifth nucleotide sequence comprises SEQ ID NO: 10; and wherein the sixth nucleotide sequence comprises SEQ ID NO:12.

5. The composition of claim 1, wherein at least one of the nucleotide sequences further encodes a leader sequence linked at the N terminus of the amino acid sequence.

6. The composition of claim 1, wherein the composition comprises at least one expression vector.

7. The composition of claim 1, further comprising a pharmaceutically acceptable excipient.

8. The composition of claim 1, wherein the first nucleotide sequence and the second nucleotide sequence encode an amino acid sequence having at least 99% identity to SEQ ID NO:13.

9. A method of treating an Ebola virus infection in a subject, the method comprising administering to the subject the composition of claim 1.

10. A method of inducing an immune response against an Ebola virus infection in a subject, the method comprising administering to the subject the composition of claim 1.

11. A method of treating an Ebola virus infection in a subject, the method comprising administering to the subject the composition of claim 7.

12. A method of inducing an immune response against an Ebola virus infection in a subject, the method comprising administering to the subject the composition of claim 7.

* * * * *